United States Patent [19]

Scholl et al.

[11] Patent Number: 5,569,721
[45] Date of Patent: Oct. 29, 1996

[54] SILICA-FILLED RUBBER COMPOUNDS CONTAINING MERCAPTOALKYL SILYL ETHERS AND GUANIDINES

[75] Inventors: Thomas Scholl, Bergisch Gladbach; Hermann-Josef Weidenhaupt, Nörvenich, both of Germany

[73] Assignee: Bayer Aktiengesellschaft, Leverkusen, Germany

[21] Appl. No.: 436,650

[22] Filed: May 8, 1995

[30] Foreign Application Priority Data

May 18, 1994 [DE] Germany ............... 44 17 354.7

[51] Int. Cl.⁶ .................... C08C 19/20; C08C 19/22
[52] U.S. Cl. ................ 525/332.7; 525/342; 525/374
[58] Field of Search .................................. 525/332.7

[56] References Cited

FOREIGN PATENT DOCUMENTS 1599395 10/1990 U.S.S.R. .

Primary Examiner—Christopher Henderson
Attorney, Agent, or Firm—Connolly & Hutz

[57] ABSTRACT

Rubber compounds containing at least one rubber, a crosslinking agent, a silica-containing filler, optionally other rubber auxiliaries and at least one of the compounds corresponding to formulae (I) and (II):

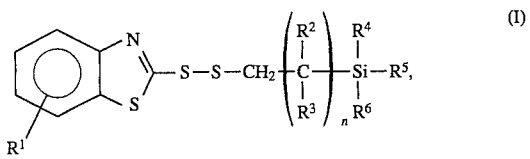

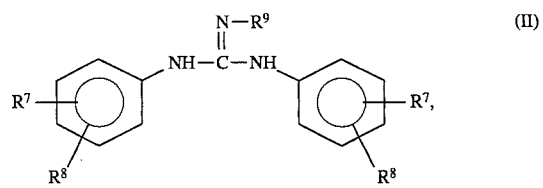

compound (I) being used in quantities of 0.1 to 15% by weight and compound (II) being used in quantities of 0.05 to 5% by weight, based on the quantity of the particular rubber used, and their use for the production of rubber vulcanizates.

4 Claims, No Drawings

SILICA-FILLED RUBBER COMPOUNDS CONTAINING MERCAPTOALKYL SILYL ETHERS AND GUANIDINES

FIELD OF THE INVENTION

This invention relates to silica-filled rubber compounds which, in addition to rubber, contain silica-containing fillers, crosslinking agents, optionally other rubber auxiliaries and special mercaptoalkyl silyl ethers and guanidines. The rubber compounds according to the invention are used for the production of rubber compounds which are distinguished by improved vulcanization behavior, more particularly by faster complete vulcanization and by a long processing time at relatively high temperatures.

BACKGROUND AND PRIOR ART

It is known that silica-filled rubber vulcanizates differ clearly in their crosslinking behavior from rubber compounds filled with carbon black. Complete vulcanization is significantly delayed and the crosslink density is too low for practical application. Accordingly, an activator, for example a mercaptopropyl silyl ether or bis-(trialkoxysilylpropyl)-tetrasulfide, generally has to be added. By contrast, mercaptopropyl silyl ethers have the unpleasant property of considerably shortening the processing time of the rubber compounds under processing conditions, so that they can only be used in special cases where a long processing time is not a problem (industrial rubber particles, not tires), cf. the comparison tests in DE 2 255 577. By contrast, bis-(trialkoxysilylpropyl)-tetrasulfide (DE 2 255 577) has the disadvantage that complete vulcanization lasts a very long time so that long production times are inevitable (see the Comparison Example of the present application). In this case, combination with a compound corresponding to formula (II) leads only to an unwanted reduction in the scorch time whereas complete vulcanization is actually extended.

EP 447 066 describes special silica-filled rubber compounds containing inter alia a special silane. There are no references in this document either to the vulcanization kinetics or to the production of the silane. According to our own tests, the silanes disclosed therein shorten the scorch time and, accordingly, are industrially unsuitable for a number of applications where processing safety is an important requirement.

DE 42 33 197 describes certain benzthiazole derivatives as vulcanization accelerators which are more effective than conventional vulcanization accelerators in silica-filled rubbers, but which do not produce any significant improvement in modulus or abrasion resistance in tires.

Accordingly, there is still a need for rubber compounds, more particularly silica-filled rubber compounds, which show good vulcanization kinetics and which, after vulcanization, give rubber articles, more particularly tires, with inter alia a good modulus value and high abrasion resistance.

SUMMARY OF THE INVENTION

Accordingly, the present invention relates to rubber compounds containing at least one rubber, a crosslinking agent, a silica-containing filler, optionally other rubber auxiliaries and at least one of the compounds corresponding to formulae (I) and (II):

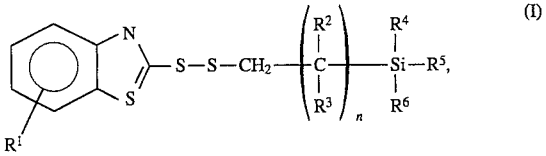

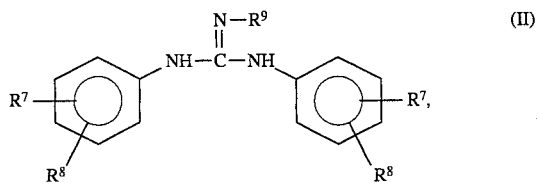

in which $R^1$ is hydrogen or $C_{1-8}$ alkyl, preferably $C_{1-4}$ alkyl, $R^2$ and $R^3$ may be the same or different and represent hydrogen, $C_{1-12}$- and preferably $C_{1-6}$-alkyl, -alkenyl or -cycloalkyl or $C_{6-12}$- and preferably $C_{6-10}$-aryl which may optionally be substituted one or more times by hydroxyl-, carboxyl- or carboxy-$C_{1-8}$-alkyl groups, $R^4$, $R^5$ and $R^6$ may be the same or different and represent $C_{1-18}$- and preferably $C_{1-6}$-alkyl, -alkenyl or -cycloalkyl, O—$C_{1-12}$- and preferably O—$C_{1-6}$-alkyl, O—$C_{6-12}$- and preferably O—$C_{6-10}$-aryl which may be substituted one or more times by O—$C_{1-8}$-alkyl groups, with the proviso that at least one of the substituents $R^4$, $R^5$ and $R^6$ is an O—$C_{1-12}$-alkyl or O—$C_{6-12}$-aryl group, n is an integer of 0 to 8 and preferably 0 to 4, $R^7$, $R^8$ and $R^9$ may be the same or different and represent hydrogen, $C_{1-12}$- and preferably $C_{1-6}$-alkyl or $C_{6-12}$- and preferably $C_{6-10}$-aryl, compound (I) being used in quantities of 0.1 to 15% by weight and compound (II) being used in quantities of 0.05 to 5% by weight, based on the quantity of the particular rubber used.

DESCRIPTION OF PREFERRED EMBODIMENTS

Compound (I) is preferably used in quantities of 0.3 to 7% by weight while compound (II) is preferably used in quantities of 0.1 to 3% by weight.

Alkyl radicals for the above formulae are, in particular, methyl, ethyl, propyl, butyl, hexyl, octyl.

Alkenyl radicals for the above formulae are, in particular, propenyl, butenyl, norbornenyl.

Cycloalkyl radicals for the above formulae are, in particular, cyclophenyl, cyclohexyl, methyl cyclohexyl.

Optionally substituted aryl radicals are, in particular, phenyl, methylphenyl, tert.butylphenyl, diphenyl.

O-alkyl radicals are, in particular, methoxy, ethoxy, n-propoxy, i-propoxy, n-butoxy, i-butoxy, amyloxy, n-hexyloxy, cyclohexyloxy, n-octoxy, i-octoxy, dodecyloxy.

Optionally substituted O-aryl radicals are, in particular, phenoxy, methylphenoxy, tert.butylphenoxy, diphenyloxy.

The following are preferred representatives of the compounds corresponding to formula (I):

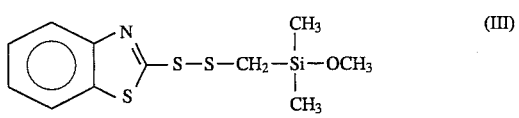

-continued

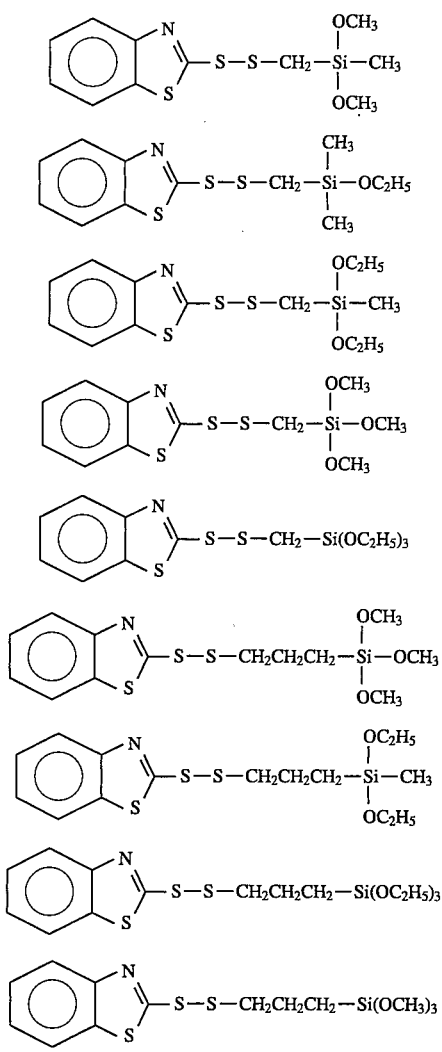

The following are preferred representatives of the compounds corresponding to formula (II):

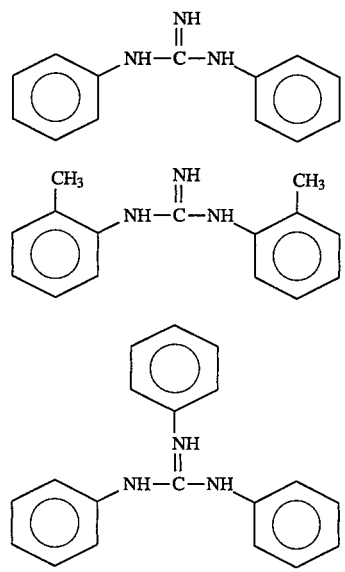

The compounds corresponding to formula (I) may be prepared by known methods:

1. Reaction of mercaptobenzthiazole sulfene chlorides with corresponding mercaptoalkyl sulfanes. Such reactions are described, for example, in Houben-Weyl, Methoden der organischen Chemie, Thieme Verlag Stuttgart, Vol. E 11, pages 140 to 142 (1985).
2. From thioimides by reaction with corresponding mercaptoalkyl silanes. This type of reaction is described, for example, in Tetrahedron Letters 41 (1970), 3551 to 3554.
3. By reaction of 2,2'-dithiobisbenzthiazole with mercaptans. Such reactions are described, for example, in Houben-Weyl, Methoden der organischen Chemie, Thieme Verlag Stuttgart, Vol. E 11, page 146 (1985).

The compounds corresponding to formula (II) and their production are known in principle (see, for example, Ullmanns Encyklopädie der technischen Chemie, 4th Edition 1976, Vol. 12, pages 416–417, Verlag Chemie, Weinheim). Suitable representatives are, for example, diphenyl guanidine, di-o-tolyl guanidine and triphenyl guanidine.

In the production of the rubber compounds according to the invention, the additives according to the invention corresponding to formula (I) and the fillers are preferably added in the first phase of the mixing process at melt temperatures of 100° to 200° C., although they may also be added at a later stage at lower temperatures (around 40° to 100° C.), for example together with sulfur and the accelerators. The additives corresponding to formula (II) are preferably added in the second phase of the mixing process (at around 40° to 100° C.).

The compounds according to the invention corresponding to formulae (I) and (II) may be added to the mixing process both in pure form and on an inert, organic or inorganic support. Preferred support materials are silicas, natural or synthetic silicates, aluminium oxide or carbon blacks.

Suitable fillers for the rubber compounds according to the invention are:

Highly disperse silicas prepared, for example, by precipitation of solutions of silicates or by flame hydrolysis of silicon halides with specific surfaces of 5 to 1000 $m^2/g$ and preferably 20 to 400 $m^2/g$ (BET surface) and with primary particle sizes of 100 to 400 nm. The silicas may even be present in the form of mixed oxides with other metal oxides, such as Al, Mg, Ca, Ba, Zn, Zr, Ti oxides.

Synthetic silicates, such as aluminium silicate, alkaline earth metal silicates, such as magnesium silicate or calcium silicate, with BET surfaces of 20 to 400 $m^2/g$ and primary particle diameters of 10 to 400 nm.

Natural silicates, such as kaolin and other naturally occurring silicas.

Glass fibers and glass fiber products (mats, strands) or glass microbeads.

Highly disperse silicas prepared by precipitation of solutions of silicates with BET surfaces of 20 to 400 $m^2/g$ are preferably used in quantities of 5 to 150 parts by weight, based on 100 parts by weight of rubber.

Carbon blacks may of course also be used as additional fillers. Suitable carbon blacks are produced by the lamp black, furnace black or gas black process and have BET surfaces of 20 to 200 $m^2/g$, such as for example SAF, ISAF, IISAF, HAF, FEF or GPF carbon blacks.

One particularly preferred embodiment is characterized by the use of 10 to 150 parts of light fillers (silicas), optionally together with 0 to 100 parts by weight of carbon black, and 0.3 to 15 parts by weight of a compound corresponding to formula (I) and 0.1 to 5% by weight of a compound corresponding to formula (II), based in either case on the rubber used, and other rubber auxiliaries, the use of 0.3 to 10% by weight of (I) and 0.1 to 3% by weight of (II) being most particularly preferred.

Besides natural rubber, synthetic rubbers are also suitable for the production of rubber vulcanizates according to the invention. Preferred synthetic rubbers are described, for example, in W. Hofmann, Kautschuktechnologie, Gentner Verlag, Stuttgart 1980. They include inter alia BR - polybutadiene
ABR - butadiene/$C_{1-4}$ alkyl acrylate copolymers
CR - polychloroprene
IR - polyisoprene
SBR - styrene/butadiene copolymers with styrene contents of 1 to 60% by weight and preferably 20 to 50% by weight
IIR - isobutylene/isoprene copolymers
NBR - butadiene/acrylonitrile copolymers with acrylonitrile contents of 5 to 60% by weight and preferably 10 to 50% by weight
HNBR - partly hydrogenated or completely hydrogenated NBR rubber
EPDM - ethylene/propylene/diene copolymers and mixtures of these rubbers. Rubbers of particular interest for the production of motor vehicle tires are anionically polymerized L-SBR rubbers with a glass temperature above −50° C. which may optionally be modified with silyl ethers or other functional groups, as described for example in EP-A 447 066, and mixtures thereof with diene rubbers.

The rubber vulcanizates according to the invention may contain other rubber auxiliaries, such as reaction accelerators, antiagers, heat stabilizers, light stabilizers, antiozonants, processing aids, plasticizers, tackifiers, blowing agents, dyes, pigments, waxes, extenders, organic acids, retarders, metal oxides and activators, such as triethanolamine, polyethylene glycol, hexanetriol, which are well known in the rubber industry.

The rubber auxiliaries are used in typical quantities determined inter alia by the particular application envisaged. Typical quantities are, for example, quantities of 0.1 to 30% by weight, based on the rubber used.

The crosslinking agents used include peroxides, sulfur, magnesium, zinc oxide, to which known vulcanization accelerators, such as mercaptobenzthiazoles and sulfenamides, thiurams and/or thiocarbonates may be added. Sulfur is preferred. The crosslinking agents and crosslinking accelerators are used in quantities of 0.1 to 10% by weight and preferably in quantities of 0.1 to 5% by weight, based on the rubber used.

Vulcanization may be carried out at temperatures of around 100° to 200° C. and preferably at temperatures of around 130° to 180° C., optionally under pressures of 10 to 200 bar.

The rubbers may be mixed with the filler and with the reinforcing additives (I) and (II) according to the invention in standard mixing units, such as mixing rolls, internal mixers and mixing extruders.

The rubber vulcanizates according to the invention are suitable for the production of molded articles, for example for the production of cable sheaths, hoses, drive belts, conveyor belts, covers for rollers, tires, shoe soles, sealing rings and damping elements.

EXAMPLES

Example 1

Production of 3-triethoxysilyl propyl dithiobenzthiazole 124.5 g (0.375 mole) of 2,2'-dithiobisbenzthiazole were chlorinated with 26.3 g (0.375 mole) of chlorine gas at 0° to 10° C. in 800 ml of chlorobenzene. 196.4 g (0.825 mole) of mercaptopropyl triethoxysilane were then added and, after stirring for 10 hours at room temperature, 51.1 g (0.75 mole) of sodium methylate were added. The precipitate was filtered off and the filtrate was freed from all volatile constituents in a high vacuum (0.1 mm). 254 g of a brown oil were obtained.

$^1$H-NMR (CDCl$_3$): 0.7–0.8 ppm (multiplet, 2 CH$_2$ protons), 1,2–1,3 ppm (triplet, 9 CH$_3$ protons), 1.8–2.0 ppm (multiplet, 2 CH$_2$ protons), 2.9–3.1 ppm (triplet, 2 CH$_2$ protons), 3.7–3.9 ppm (quartet, 6 CH$_2$ protons), 7.2–7.9 ppm (multiplet, 4 aromatic protons).

The following compound was prepared in a kneader at an internal temperature of 150° C. Sulfur and accelerator were subsequently added on mixing rolls at 50° C. For vulcanization, the compounds were heated for 25 minutes to 160° C. in heatable presses:

TABLE

|  | Comp. 1 | Comp. 2 | Comp. 3 | Comp. 4 | Comp. 5 | Ex. A | Ex. B | Ex. C |
| --- | --- | --- | --- | --- | --- | --- | --- | --- |
| E-SBR (Buna EM 1500) | 70 | | | | | | | |
| E-SBR (Buna EM 1778) | 41 | | | | | | | |
| Silica (Vulkasil S) | 50 | | | | | | | |
| Zinc oxide | 3 | | | | | | | |
| Stearic acid | 2 | | | | | | | |
| Diethylene glycol | 1.5 | | | | | | | |
| Coumarone resin | 5 | | | | | | | |
| Dioctylated diphenylamine | 1 | | | | | | | |
| Bis-(triethoxysilylpropyl)-tetrasulfide (DE 2 255 577) | 3.5 | 3.5 | — | — | — | — | — | — |
| Silane comp. 2 of EP 447 066 | — | — | — | 3.5 | 3.5 | | | |
| Compound of Ex. 1 | — | — | 3.5 | — | — | 3.5 | 3.5 | 3.5 |
| Diphenyl guanidine | — | 1.5 | — | — | 1.0 | 1.5 | 1.0 | 0.5 |
| Cyclohexylmercaptobenzthiazole sulfenamide | 1.5 | — | 1.5 | — | — | — | — | — |
| Tetramethyl thiuram disulfide | 0.1 | | | | | | | |
| Sulfur | 2 | | | | | | | |
| Vulcanization kinetics (160° C.) t-s (mins.) | 7.7 | 3.8 | 11.2 | 4.0 | 2.8 | 6.3 | 5.6 | 6.3 |
| t-90 (mins.) | 19.9 | 20.6 | 25.9 | 15.7 | 10.7 | 13.8 | 11.5 | 13.6 |
| Modulus at 300% elongation (MPa) | 7.21 | 3.89 | 7.61 | | | 8.09 | 8.25 | 7.21 |
| Strength (MPa) | 16.6 | 21.7 | 15.0 | | | 15.5 | 16.7 | 17.9 |

TABLE-continued

| | Comp. 1 | Comp. 2 | Comp. 3 | Comp. 4 | Comp. 5 | Ex. A | Ex. B | Ex. C |
|---|---|---|---|---|---|---|---|---|
| Elasticity (%) | 534 | 760 | 489 | | | 482 | 502 | 559 |
| Hardness (Shore A/23° C. | 65 | 62 | 65 | | | 66 | 66 | 65 |
| Elasticity (%/70° C.) | 60 | 53 | 59 | | | 59 | 60 | 58 |
| Abrasion (DIN 53 516) | 134 | 133 | 122 | | | 123 | 122 | 122 |

It can be seen that the rubber compounds containing the additive combinations according to the invention (Examples A, B and C) have a distinctly higher vulcanization rate (measured as t-90=time taken to reach 90% of the end point of crosslinking in minutes). By contrast, the time elapsing to the beginning of crosslinking (t-s in minutes) is at a very high level.

It can also be seen that the combination of a compound (II) (diphenyl guanidine) with bis-(triethoxy-silylpropyl)-tetrasulfide (Comparison 2) only produces disadvantages in relation to the combination of the same compound with sulfenamide accelerator (less time to the beginning of crosslinking, no positive effect on the vulcanization rate; lower crosslink density, as observed in the lower modulus at 300% and lower hardness). Finally, Comparison 4 shows that silane 2 of EP 447 066, which is structurally related to the compounds (I), gives rise to far less favorable scorch behavior than the combination according to the invention. The combination with a compound corresponding to formula (II) (diphenyl guanidine) leads to a further unacceptable reduction in the scorch time (Comparison 5).

We claim:

1. Rubber compounds comprising at least one natural or synthetic rubber, a crosslinking agent, a silica-containing filler, and compounds corresponding to the formulae (I) and (II):

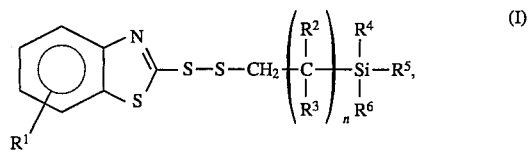

(I)

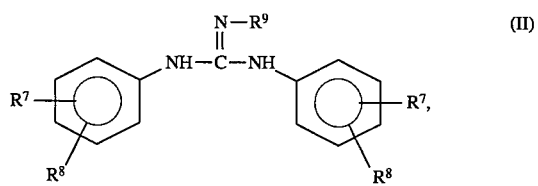

(II)

in which $R^1$ is hydrogen or $C_{1-8}$ alkyl, $R^2$ and $R^3$ may be the same or different and represent hydrogen, $C_{1-12}$-alkyl, -alkenyl or -cycloalkyl or $C_{6-12}$-aryl which may optionally be substituted one or more times by hydroxyl-, carboxyl- or carboxy-$C_{1-8}$-alkyl groups, $R^4$, $R^5$ and $R^6$ may be the same or different and represent $C_{1-18}$-alkyl, -alkenyl or -cycloalkyl, O—$C_{1-12}$-alkyl, O—$C_{6-12}$-aryl which may be substituted one or more times by O—$C_{1-8}$-alkyl groups, with the proviso that at least one of the substituents $R^4$, $R^5$ and $R^6$ is an O—$C_{1-12}$-alkyl or O—$C_{6-12}$-aryl group, n is an integer of 0 to 8, $R^7$, $R^8$ and $R^9$ may be the same or different and represent hydrogen, $C_{1-12}$-alkyl or $C_{6-12}$-aryl, and wherein compound (I) is present in quantities of 0.1 to 15% by weight and compound (II) is present in quantities of 0.05 to 5% by weight, based on the amount of rubber.

2. The rubber compound of claim 1, wherein $R^1$ is H or $C_{1-4}$-alkyl, $R^2$ and $R^3$ are H or $C_{1-6}$-alkyl, -alkenyl or -cycloalkyl or $C_{6-12}$-aryl, $R^4$, $R^5$ and $R^6$ are $C_{1-6}$-alkyl, -alkenyl or -cycloalkyl, O—$C_{1-6}$-alkyl or O—$C_{6-10}$aryl, n is an integer of 0 to 4, and $R^7$, $R^8$ and $R^9$ are H or $C_{1-6}$-alkyl or $C_{6-10}$-aryl.

3. The rubber compound of claim 1, which contains carbon black.

4. The rubber compound of claim 1, which contains other rubber auxiliaries selected from the group consisting of accelerators, antiagers, heat stabilizers, light stabilizers, antioxonants, processing aids, plasticizers, tackifiers, blowing agents, dyes, pigments, waxes, extenders, organic acids, retarders, metal oxides, and activators.

* * * * *